(12) United States Patent
Alenfall et al.

(10) Patent No.: US 8,420,376 B2
(45) Date of Patent: Apr. 16, 2013

(54) **USE OF *LACTOBACILLUS* FOR TREATMENT OF VIRUS INFECTIONS**

(75) Inventors: Jan Alenfall, Lomma (SE); Anna Berggren, Flyinge (SE); Carola Rask, Mölndal (SE); Agnes Wold, Mölndal (SE)

(73) Assignee: Probi AB, Lund (SE)

( * ) Notice: Subject to any disclaimer, the term of this patent is extended or adjusted under 35 U.S.C. 154(b) by 856 days.

(21) Appl. No.: 11/992,488

(22) PCT Filed: Oct. 6, 2006

(86) PCT No.: PCT/SE2006/001138
§ 371 (c)(1),
(2), (4) Date: May 6, 2009

(87) PCT Pub. No.: WO2007/040445
PCT Pub. Date: Apr. 12, 2007

(65) Prior Publication Data
US 2010/0034877 A1 Feb. 11, 2010

(30) Foreign Application Priority Data

Oct. 6, 2005 (SE) ...................................... 0502209
Oct. 7, 2005 (SE) ...................................... 0502250

(51) Int. Cl.
*C12N 1/20* (2006.01)
(52) U.S. Cl.
USPC ...................................................... 435/252.9
(58) Field of Classification Search .................... None
See application file for complete search history.

(56) References Cited

U.S. PATENT DOCUMENTS

| 4,983,163 | A | 1/1991 | Winans et al. | |
|---|---|---|---|---|
| 6,830,750 | B1 * | 12/2004 | Naruszewicz | 424/93.45 |
| 2004/0022775 | A1 | 2/2004 | Reid et al. | |
| 2006/0182727 | A1 * | 8/2006 | Yamahira et al. | 424/93.45 |

FOREIGN PATENT DOCUMENTS

| JP | 10-167972 | 6/1998 |
|---|---|---|
| JP | 2002-537867 | 11/2002 |
| JP | 2004-507265 | 3/2004 |
| JP | 2004-121073 | 4/2004 |
| WO | WO00/53202 A1 | 9/2000 |
| WO | WO00/78322 A2 | 12/2000 |
| WO | WO 2004/087893 | 10/2004 |
| WO | WO2004/103083 A1 | 12/2004 |
| WO | WO2005/007834 A1 | 1/2005 |

OTHER PUBLICATIONS

Molin et al., 2006, *Lactobacillus plantarum* 299v, retrieved from www.proviva.com/upload/pdf/dokumentation.pdf.*
Molin et al., *Lactobacillus plantarum* 299v, retrieved from www.proviva.com/upload/pdf/dokumentation.pdf.*
Douglas et al., Journal of Immunology, vol. 99, No. 2, pp. 297-303, 1967.*
Extended European Search Report for corresponding Application No. PCT/SE2006001138, dated Dec. 29, 2009.
Hereas, M.V. et al., Immunomodulatory effects of *Lactobacillus plantarum* colonizing the intestine of gnotobiotic rats, *Clin Exp Immunol* May 1999; pp. 283-290, vol. 116, No. 2, Blackwell Science Ltd., UK.
Cunningham-Rundles, Susanna, "Probiotics and Immune Response", The American Journal of Gastroenterology, 2000, vol. 95, No. 1, pp. S22-S25, abstract.
Uchida, Shinsuke et al., "Studies on virus-inhibiting substances of bacterial origin", Kobe J. Med Sci., Jun. 1978, vol. 24, pp. 91-98.
Parra, M.D. et al., "Daily ingestion of fermented milk containing *Lactobacillus casei* DN114001 improves innate defense capacity in healthy middle-aged people", J. Physiol. Biochem., 2004, vol. 60, No. 2, pp. 85-92.
Anna Berggren et al., *Randomised, double-blind and placebo-controlled study using new probiotic lactobacilli for strengthening the body immune defence against viral infections*, 50(3) Eur. J. Nutr. 203-10 (2011).
Japanese Office Action mailed on Apr. 24, 2012, in corresponding Japanese Patent Application 2008-534490.
Japanese Office Action mailed on Dec. 18, 2012, in corresponding Japanese Patent Application 2008-534490.

* cited by examiner

*Primary Examiner* — Allison Ford
*Assistant Examiner* — Yvonne Pyla
(74) *Attorney, Agent, or Firm* — Buchanan Ingersoll & Rooney

(57) ABSTRACT

The present technology relates to the use of at least one strain of probiotic bacteria selected from *Lactobacillus* for the manufacture of a pharmaceutical composition for the treatment and/or prevention of a virus infection.

16 Claims, 13 Drawing Sheets

Fig. 1

|  | Wash out period (Week) | | Study period (Week) | | | | | Post study period (Week) | |
|---|---|---|---|---|---|---|---|---|---|
|  | -2 | -1 | 1 | 2 | 3 | 4 | 5 | +1 | +2 |
| *L. plantarum* | 0/7 | 1/7 | 3/7 | 2/7 | 3/7 | 2/7 | 1/7 | 1/7 | 0/7 |
| *L. Heal 19* | 0/7 | 1/7 | 1/7 | 2/7 | | | | 2/7 | 1/7 |
| *L. fermentum* | 0/7 | 0/7 | 0/7 | 0/7 | | | | 1/7 | 0/7 |
| *L. paracasei* | 0/7 | 0/7 | 1/7 | 0/7 | | | | 0/7 | 0/7 |
| *L. gasseri* | 0/7 | 0/7 | 3/7 | 1/7 | | | | 4/7 | 0/7 |
| *L. rhamnosus* | 1/7 | 1/7 | 0/7 | 0/7 | | | | 1/7 | 0/7 |
| *P. lundensis* | 1/6 | 1/6 | 1/6 | 1/6 | | | | 0/6 | 0/6 |
| Placebo | 0/9 | 0/9 | 2/9 | 3/9 | 1/8 | 1/8 | 0/8 | 0/8 | 0/8 |

Fig. 2.

|  | CD4+ T cells (x 10³) | CD8+ T cells (x 10³) | NKT cells (x 10³) |
|---|---|---|---|
| *L. plantarum* | 647 (92) | 318 (37) | 64 (17) |
| *L. Heal 19* | 817 (105) | 328 (43) | 56 (19) |
| *L. fermentum* | 907 (82) | 479 (51) | 87 (21) |
| *L. paracasei* | 794 (87) | 321 (64) | 98 (21) |
| *L. gasseri* | 767 (54) | 497 (110) | 111 (39) |
| *L. rhamnosus* | 775 (109) | 387 (50) | 109 (22) |
| *P. lundensis* | 731 (65) | 468 (84) | 87 (29) |
| Placebo | 650 (43) | 300 (34) | 107 (30) |

Figure 3.

| | % CD4+CD25+ of lymphocytes | % CD8+CD25+ of lymphocytes | % CD4+HLA-DR+ of lymphocytes | % CD8+HLA-DR+ of lymphocytes | GMFI CD45RO on CD4+ T cells | GMFI CD45RO on CD8+ T cells |
|---|---|---|---|---|---|---|
| *L. plantarum* | 10 (0,90) | 0,83 (0,19) | 4,3 (0,69) | 5,0 (1,8) | 53 (10) | 27 (5,6) |
| *L. Heal 19* | 17 (2,6) | 1,5 (0,40) | 4,4 (1,2) | 6,6 (3,3) | 126 (39) | 61 (15) |
| *L. fermentum* | 15 (0,98) | 1,5 (0,31) | 4,4 (0,51) | 7,0 (1,1) | 71 (13) | 36 (5,6) |
| *L. paracasei* | 17 (1,1) | 1,7 (0,73) | 8,5 (4,7) | 6,1 (1,6) | 83 (13) | 50 (17) |
| *L. gasseri* | 15 (2,0) | 1,3 (0,26) | 3,3 (0,60) | 5,2 (1,3) | 110 (96) | 45 (14) |
| *L. rhamnosus* | 14 (0,60) | 1,3 (0,13) | 3,0 (0,34) | 5,2 (1,3) | 80 (24) | 40 (11) |
| *P. lundensis* | 18 (4,1) | 4,0 (2,3) | 10 (6,7) | 9,4 (2,4) | 65 (9,4) | 38 (3,5) |
| Placebo | 13 (1,0) | 2,6 (1,4) | 4,2 (0,59) | 6,8 (3,5) | 39 (8,2) | 23 (5,1) |

A
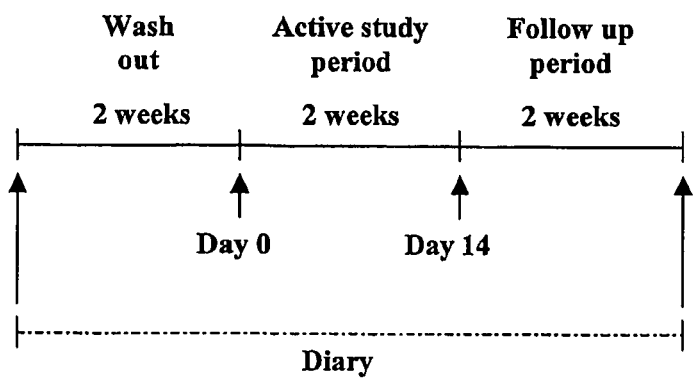
B
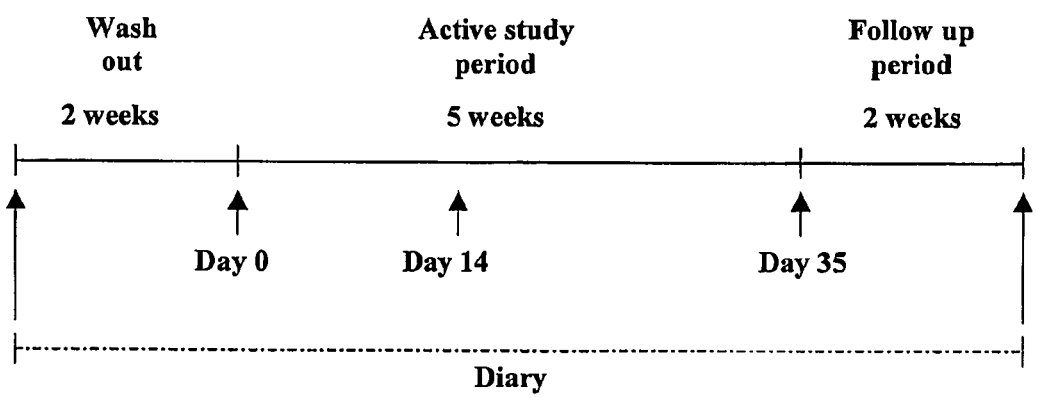
Fig. 4

Fig. 5
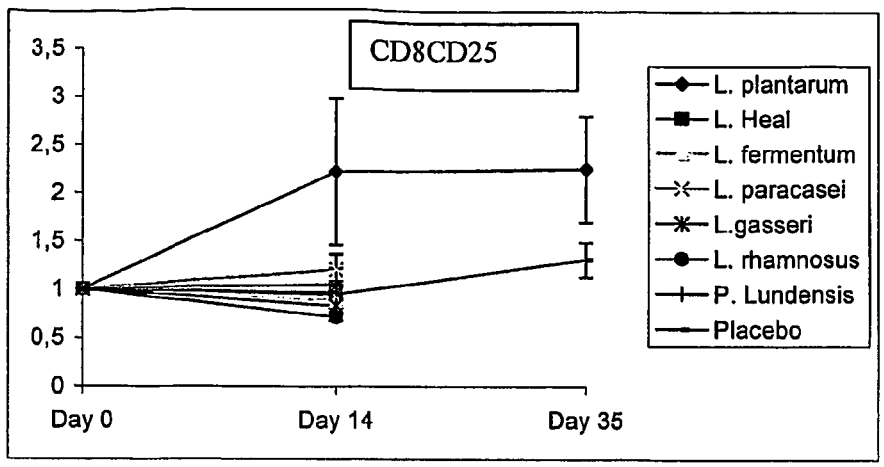
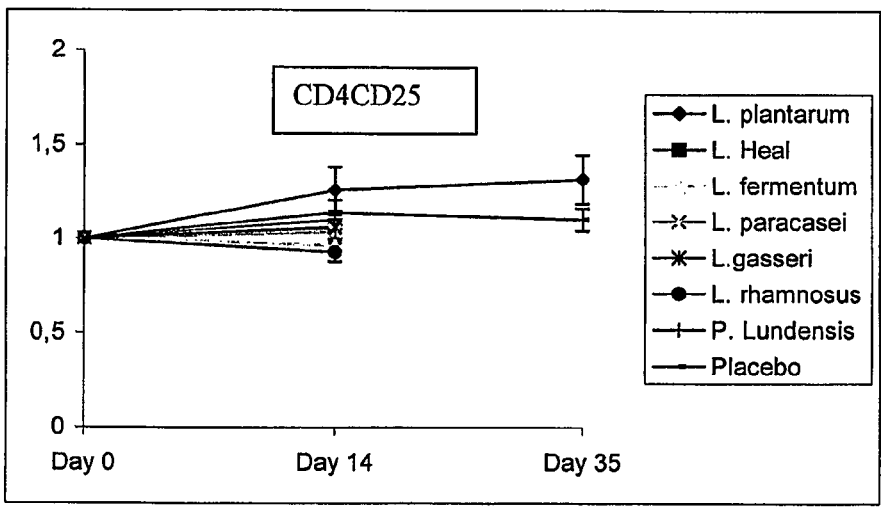
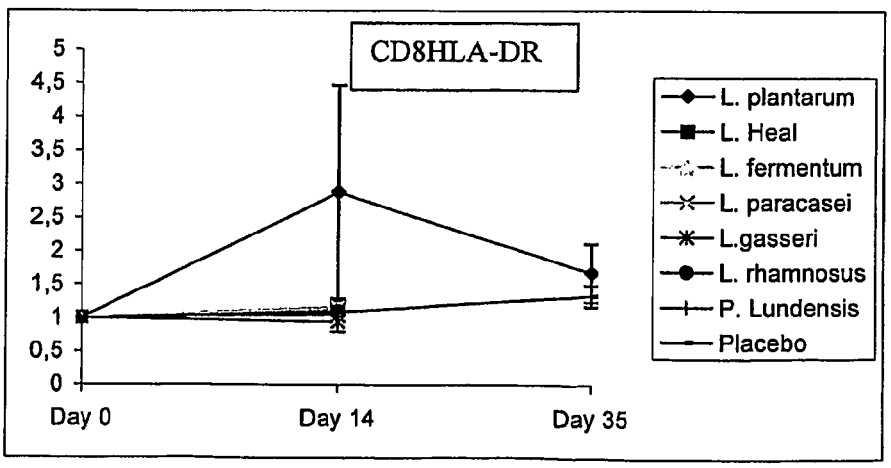

Fig. 5 (continued)
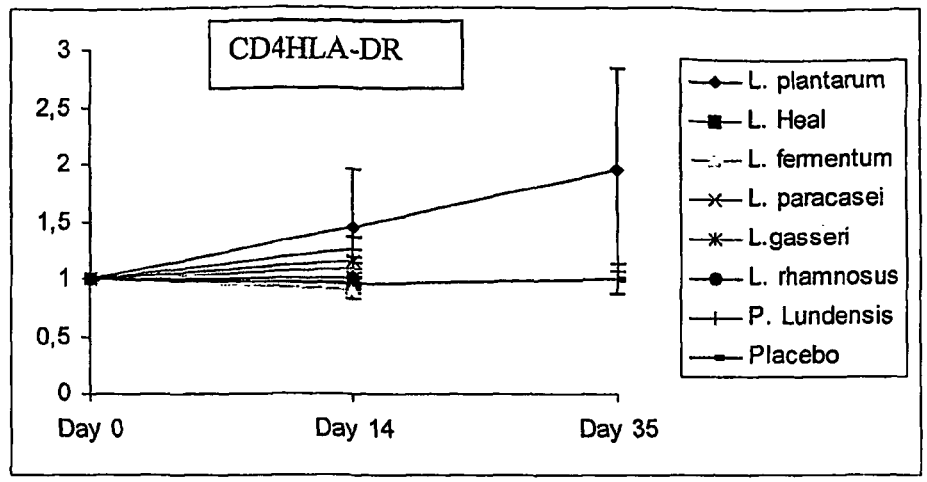
Fig. 6.
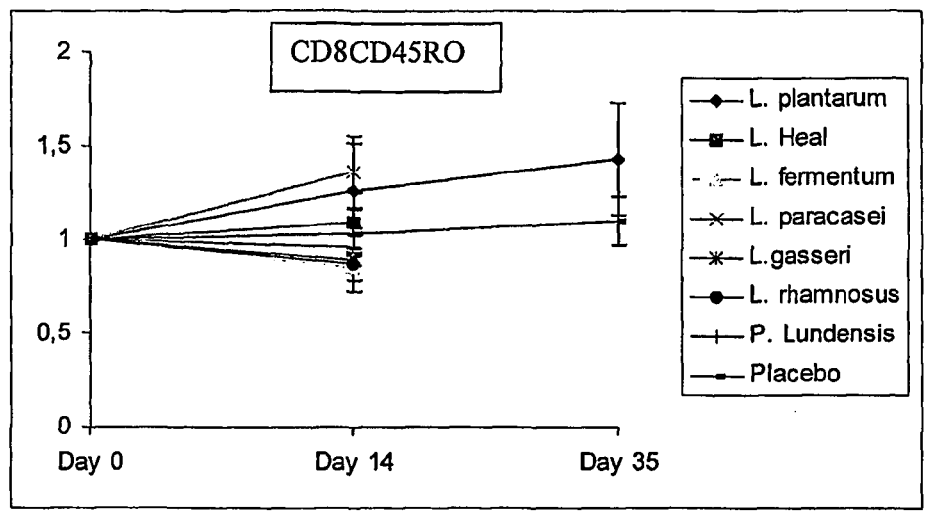
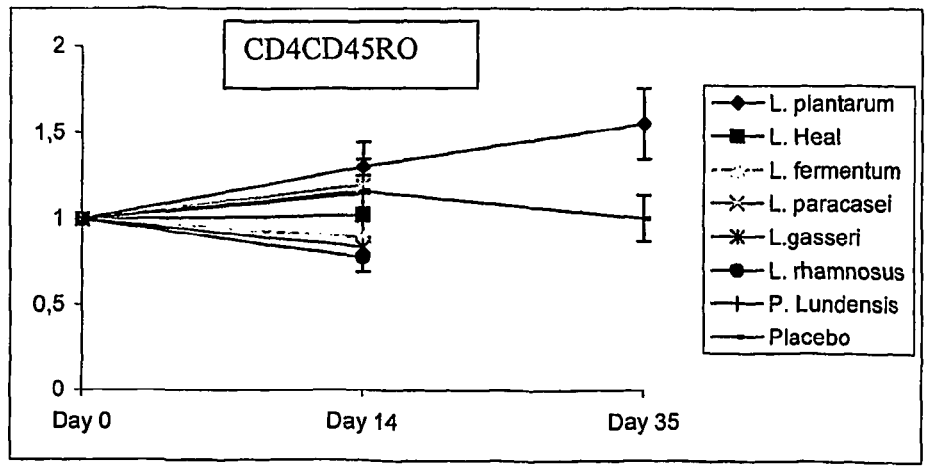

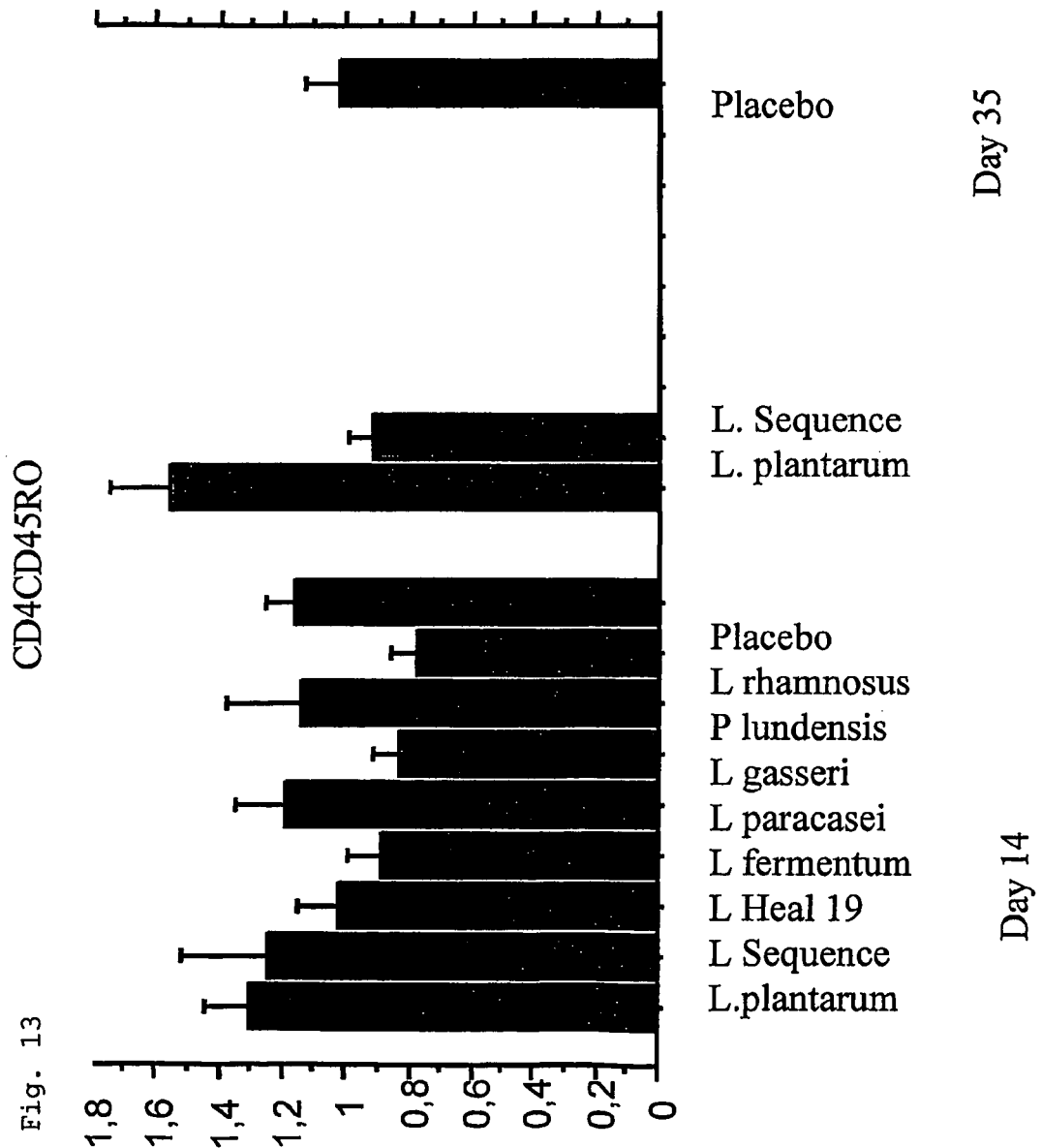

USE OF *LACTOBACILLUS* FOR TREATMENT OF VIRUS INFECTIONS

FIELD OF THE INVENTION

The present invention relates to the use of at least one strain of probiotic bacteria selected from *Lactobacillus* for the manufacture of a pharmaceutical composition for the treatment and/or prevention of a virus infection.

BACKGROUND ART

Probiotic bacteria are defined as live micro-organisms which when administered in adequate amounts beneficially affect the host. Lactobacilli and bifidobacteria are the most frequently used bacteria in probiotic products. These bacteria are generally safe, as are probiotics based on these organisms. The lack of pathogenicity extends across all age groups and to immunocompromised individuals. Intake of different probiotic bacteria has been shown to have clinical benefits in various physiologic or pathologic situations. The most clear cut effects have been shown in diarrhea caused by antibiotic therapy or rotavirus infection. There are also studies showing positive clinical effects in inflammatory bowel diseases, atopic dermatitis and hypercholesterolemia after intake of probiotic bacteria. The mechanism, by which probiotic bacteria contribute to these clinical improvements are not clear. In vitro human, as well as both in vivo and in vitro animal studies have shown that different species of lactobacilli affects the innate and acquired immune system in many different ways. Clinical studies have mainly shown stimulation of the innate cellular immune system and enhancement of humoral immune responses to natural infections and systemic or oral immunisation. Regarding effects of the innate immune system, increased phagocytic activity of polymorphonuclear cells (PMN) and increased NK cell tumor killing activity have been reported. To our knowledge, there are no clinical studies showing effects on the specific cellular immune system after intake of probiotic bacteria.

According to the present invention the effects on the innate and acquired immune system following daily intake of lactobacilli or the Gram-negative bacteria *P. lundensis* have been thoroughly investigated. Interestingly, it has been observed an activation of the specific cellular immune system in subjects receiving *L. plantarum* and indications of such in subjects receiving *L. paracasei*. Moreover, immunity-enhancing effects on the innate immune system, such as expansion of the NKT cell population and increased phagocytic activity were observed in subjects receiving different lactobacilli species. Intake of the Gram-negative bacteria *P. lundensis* had no effects, whatsoever, on the different immune parameters measured according to the experiments described herein.

The development of antibiotic resistance and failures in various treatment of infections have risen an increased interesting in probiotics as an alternative tool. There might be a need for a probiotic functional food product targeting the common cold problem. It is clear in terms of the high number of incidence of cold infections every year. Traditionally foods with high levels of vitamin C have been taken to try to reduce the incidence of common cold. On the market there are a number of different products claiming some effect on the immune system.

The present application will aim to study if a probiotic functional food product after regular administrations could affect the common cold symptoms in a similar way and thus can be an alternative solution for this problem in the general community.

SUMMARY OF THE INVENTION

An object of the present invention is the use of at least one strain of probiotic bacteria selected from *Lactobacillus* for the manufacture of a pharmaceutical composition for the treatment and/or prevention of a virus infection.

Another object of the present invention is a method for treatment and/or prevention of a virus infection, wherein at least one strain of probiotic bacteria selected from *Lactobacillus* is administered to an individual.

BRIEF DESCRIPTION OF THE DRAWINGS

FIG. 1 shows the numbers of volunteers reporting any minor adverse gastrointestinal effects during the trial.

FIG. 2 shows base line numbers (day 0) of different lymphocytes per ml blood (mean±(SEM))

FIG. 3 shows base line (day 0) percentages or GMFI (mean±(SEM)) of lymphocytes positive for different cell activation and memory markers.

FIG. 4. Subjects were randomly assigned to nine different study groups. The trial started with a wash out period of two weeks. Thereafter, the active study period followed. During this period, the subjects consumed one dose of study product per day for 14 (*L. plantarum* Heal 19, *L. fermentum*, *L. paracasei*, *L. gasseri*, *L. rhamnosus*, *P. lundensis* groups) or 35 days (*L. plantarum* 299v and placebo group). Each dose contained $10^{10}$ coloni forming units (CFU) (lactobacilli groups) or $10^9$ CFU bacteria (*P. lundensis* group).

FIG. 5. Percentages of lymphocytes expressing the activation phenotypes CD8CD25, CD8HLA-DR, CD4CD25 and CD4HLA-DR was analysed by flowcytometry. Group means (±SEM) based on individual ratios, day 14/day 0 and day 35/day 0 (for *L. plantarum* and placebo group only) is shown.

FIG. 6. Percentages of lymphocytes expressing the memory phenotypes CD8CD45RO and CD4CD45RO was analysed by flowcytometry. Group means (±SEM) based on individual ratios, day 14/day 0 and day 35/day 0 (for *L. plantarum* and placebo group only) is shown.

FIG. 13 shows the ratio of lymphocytes expressing the activation phenotypes CD4CD45RO from experiment 2.

DETAILED DESCRIPTION OF THE INVENTION

Figure 7:
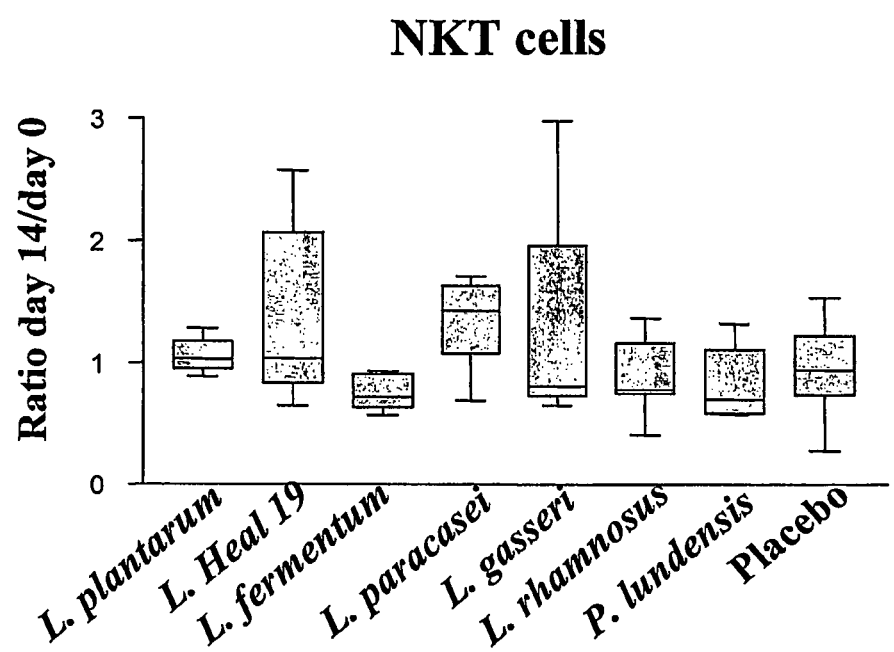
FIG. 7. Percentages of lymphocytes positive for the NKT cell markers (CD56CD16CD3) was analysed by flowcytometry. Group calculations are based on individual ratios (day 14/day 0).

The *Lactobacillus* used according to the invention may be selected from, but not limited to, the group consisting of

*Lactobacillus plantarum, Lactobacillus rhamnsosus, Lactobacillus fermentum, Lactobacillus paracasei* and *Lactobacillus gasseri*.

The *Lactobacillus plantarum* used according to the invention may be selected from, but not limited to, the group consisting of *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316.

The *Lactobacillus paracasei* used according to the invention may be selected from, but not limited to, the group consisting of *Lactobacillus paracasei* 8700:2, DSM 13434, and *Lactobacillus paracasei* 02A, DSM13432. The *Lactobacillus gasseri* used according to the invention may be selected from, but not limited to, *Lactobacillus gasseri* VPG44, DSM 16737.

Other probiotic bacterial strains, than the ones explicitly disclosed herein, may naturally be used according to the present invention and are within the scope of the invention as long as they provide the desired effects, i.e. have a preventive effect on a virus infection or alleviates a virus infection.

In an embodiment of the invention at least two strains of probiotic bacteria are used in the pharmaceutical composition. Said at least two strains are intended to be administered sequentially or simultaneously. Thus, the strains may be administered in a mixture in one composition or they may be administered in a sequence separately in different compositions.

According to the invention it is possible to treat virus infections. Treatable virus infections are i.e. those caused by a virus selected from, but not limited to, the group consisting of herpes simplex I virus, herpes simplex II virus, herpes zoster virus, common cold virus, rhinovirus, adenovirus, parainfluenza virus, respiratory syncytial virus, enterovirus and coronavirus. Any other virus infection, not specifically mentioned here, that the probiotic bacteria have an effect on are also within the scope of the present invention. It is known that there are many different viruses and forms thereof that cause a common cold. All such viruses are within the scope of the present invention.

In the present context the word "treatment and/or prevention" includes a prophylactic treatment of an individual, i.e. the treatment with the probiotic bacteria is started before the disease or virus infection has developed in order to prevent the disease/infection, as well as a treatment of a disease/infection that already has developed in an individual. In the latter case an alleviation of the symptoms is for instance expected or the general condition of the patient is enhanced or the patient is cured from the disease/infection faster. Thus, the individual may be a person at risk for developing an infection or not or an infection has already developed in the patient.

In an embodiment of the invention each of said strain(s) is present in the pharmaceutical composition in an amount of, but not limited to, about $1 \times 10^6$ to about $1 \times 10^{14}$ CFU, preferably from about $1 \times 10^8$ to about $1 \times 10^{12}$, and more preferably from about $1 \times 10^9$ to about $1 \times 10^{11}$.

The pharmaceutical composition according to the invention may e.g. be a liquid formulation or a solid formulation.

When the pharmaceutical composition is a solid formulation it may be formulated as a tablet, a sucking tablet, a sweet, a chewing tablet, a chewing gum, a capsule, a sachet, a powder, a granule, a coated particle, a coated tablet, an enterocoated tablet, an enterocoated capsule, a melting strip or a film.

When the pharmaceutical composition is a liquid formulation it may be formulated as an oral solution, a suspension, an emulsion or syrup. Said composition may further comprise a carrier material independently selected from, but not limited to, the group consisting of oat meal gruel, lactic acid fermented foods, resistant starch, dietary fibres, carbohydrates, proteins, and glycosylated proteins.

In an embodiment of the invention said pharmaceutical composition is a medical food, a functional food, a dietary supplement, a nutritional product or a food preparation.

The pharmaceutical composition according to the invention, used according to the invention or produced according to the invention may also comprise other substances, such as an inert vehicle, or pharmaceutical acceptable adjuvants, carriers, preservatives etc., which are well known to persons skilled in the art.

The wording "pharmaceutical composition" does not necessarily need to be a pharmaceutical composition in its normal sense but may be formulated as a food composition, a dietary supplement, a functional food, a medical food or a nutritional product as long as the required effect is achieved, i.e. treatment or prevention of virus infections. Said food composition may be chosen from the group consisting of beverages, yoghurts, juices, ice creams, breads, biscuits, cereals, health bars, spreads and nutritional products. The food composition may further comprise a carrier material, wherein said carrier material is chosen from the group consisting of oat meal gruel, lactic acid fermented foods, resistant starch, dietary fibres, carbohydrates, proteins and glycosylated proteins.

Thus, the use of a composition according to the invention may be very beneficial in the sense of being usable prophylactically, i.e. before the virus infection has developed. Since the pharmaceutical composition used is not necessarily a pharmaceutical composition in its normal sense, but can also be a dietary supplement or functional food, it is very convenient for a normal healthy individual to take to composition of the invention prophylactically.

EXAMPLES

Example 1

Subjects and Trial Criteria

Fifty-seven apparently healthy volunteers within the age range 18-55 years (median, 26 years) were selected for this blind placebo controlled study. Subjects were randomly assigned to eight groups, receiving either one of the following Gram-positive bacteria, *L. plantarum* 299v (n=7), *L. plantarum* Heal 19 (n=7), *L. fermentum* 35D (n=7), *L. paracasei* 8700:2 (n=7), *L. gasseri* VPG44 (n=7), *L. rhamnosus* 271 (n=7), or the Gram-negative bacteria, *P. lundensis* (n=7) or placebo (n=10). The dose of bacteria was $10^{10}$ bacteria/day for lactobacilli and $10^9$ bacteria/day for *P. lundensis*. The control group took skim milk powder (1 g). Depending on the group, the study had a duration period of 6 or 9 weeks consisting of two weeks wash out period, 2 or 5 weeks active study period and 2 weeks follow up period (FIG. 4). Each subject was supplied with a list of products containing probiotic products, which should not be consumed during the whole study period. Peripheral blood samples were withdrawn from subjects by venipuncture at two or three time points, day 0, day 14 and day 35. A diary, in which each subject stated adverse effects, health conditions and confirmed intake of study product, was kept during the trial.

Flow Cytometry

Phenotypic analysis of lymphocytes in whole blood was performed by flow cytometry. The following anti-human monoclonal antibodies were used as surface markers for different cell populations: CD3 FITC (SK7), CD4 APC (SK3), CD8 PerCP (SK1), CD19 PerCP (SJ25C1), CD56 PE (MY31), CD16 PE (B73.1), and CD5 FITC (L17F12). Following anti-human monoclonal antibodies were used for detection of different activation and memory markers: CD25 FITC (2A3), HLA-DR PE (L243), CD45RO PE (UCHL-1), CD38 PE (HB7), CD27 PE (L128), and CD11b PE (D12). All antibodies were purchased from Becton-Dickinson (Erembodegum, Belgium). Whole blood (100 µl) was incubated with antibodies (10 µl/antibody) for 30 min at 4° C. in the dark. Thereafter, 2 ml of FACS lysing solution (Becton-Dickinson) was added and incubated for 15 min at 20° C. in the dark. Cells were washed by adding 3 ml FACSFlow and centrifuged at 300×g for 5 min. Washed cells were resuspended in 200 µl FACSFlow and analysed on a FacsCalibur (Becton-Dickinson) with CellQuest software.

Phagocytosis Assay

The phagocytic activity of granulocytes and monocytes were quantified with PHAGOTEST™ (Orpegen Pharma, Heidelberg, Germany) according to manufacturers instruction with some modifications. Briefly, 20×10⁶ FITC labelled *E. coli* or FITC labelled *S. aureus* was added to pre-cooled whole blood (100 µl). Blood cells and bacteria were incubated on 37° C. for 10 FacsCalibur with CellQuest software.

Calculations

Individual changes regarding different immune parameters were determined by calculating the ratio between the individual values obtained at day 14 and day 0, or the values at day 35 and day 0. These ratios were used for all group calculations and statistics.

Statistics

All statistical analyses were performed using Statview. Mann-Whitney U test were used to compare different groups.

Results

Clinical Observations

Fifty-four out of fifty-seven volunteers completed the study. Two persons were excluded due to infection and antibiotic treatment (one in the placebo group and one in the group receiving *P. lundensis*). One person was excluded day 16 due to pregnancy (placebo group). Only mild adverse gastrointestinal side effects were reported following intake of study products (FIG. 1).

Intake of Lactobacilli Activates T Cells

There were great baseline (day 0) individual variations regarding activation markers on $CD4^+$ and $CD8^+$ T cells. The baseline percentages of cells expressing different cell surface markers are shown in FIG. 2. No significant differences were observed between different groups at this time point. Since huge inter-individual variations were observed, it was chosen to compare ratio values at day 14 and day 35 compared to day 0 for each individual. All calculations and comparisons were done on these ratio values (day 14/day 0 and day 35/day 0). After 14 days of intake of study product containing *L. plantarum* 299v there was an approximately twofold increase of the expression of the activation marker CD25 on $CD8^+$ T cells (p=0.01) (FIG. 5). There was also a strong, although not significant (p=0.12), indication of upregulation of HLA-DR on $CD8^+$ cells following *L. plantarum* 299v intake. In addition, it was also observed a tendency towards activation of $CD4^+$ T cells after *L. plantarum* 299v intake. Intake of the other lactobacilli species included in this study, as well as the Gram-negative bacteria *P. lundensis* activated neither $CD8^+$ nor $CD4^+$ T cells. However, there was a tendency that intake of *L. paracasei* did increase the expression of HLA-DR on $CD4^+$ T cells (p=0.18).

Intake of Lactobacilli Induces a Memory Phenotype of $CD4^+$ T Cells

Geometric means of the fluorescence intensity (GMFI) of the expression of CD45RO on CD4+ and CD8+ T cells were compared between groups receiving different study products. As above, group calculations based on individual ratio values (day 14/day 0 and day 35/day 0) were used for comparisons. After 35 days of intake of study product containing *L. plantarum* 299v the CD45RO GMFI on CD4+ T cells increased significantly (p=0.03). There was also a tendency towards increased CD45RO expression on CD8+ T cells following intake of *L. plantarum* (FIG. 6). Moreover, intake of *L. paracasei* seems to have a positive effect on upregulation of CD45RO on CD8+ T cells (p=0.10) (FIG. 6).

Effect on Different Cell Populations Following Intake of Study Product

Following intake of *L. pararcasei* there was an increase in the percentage of lymphocytes being identified as NKT cells (P=0.06) (FIG. 7). Relative increase/decrease compared to day 0 could not be detected regarding other cell populations, such as CD4+ T cells, CD8+ T cells, B cells, B-1 cells (CD19+CD5+), NK cells, granulocytes and monocytes.

Phagocytic Activity

Figure 8:
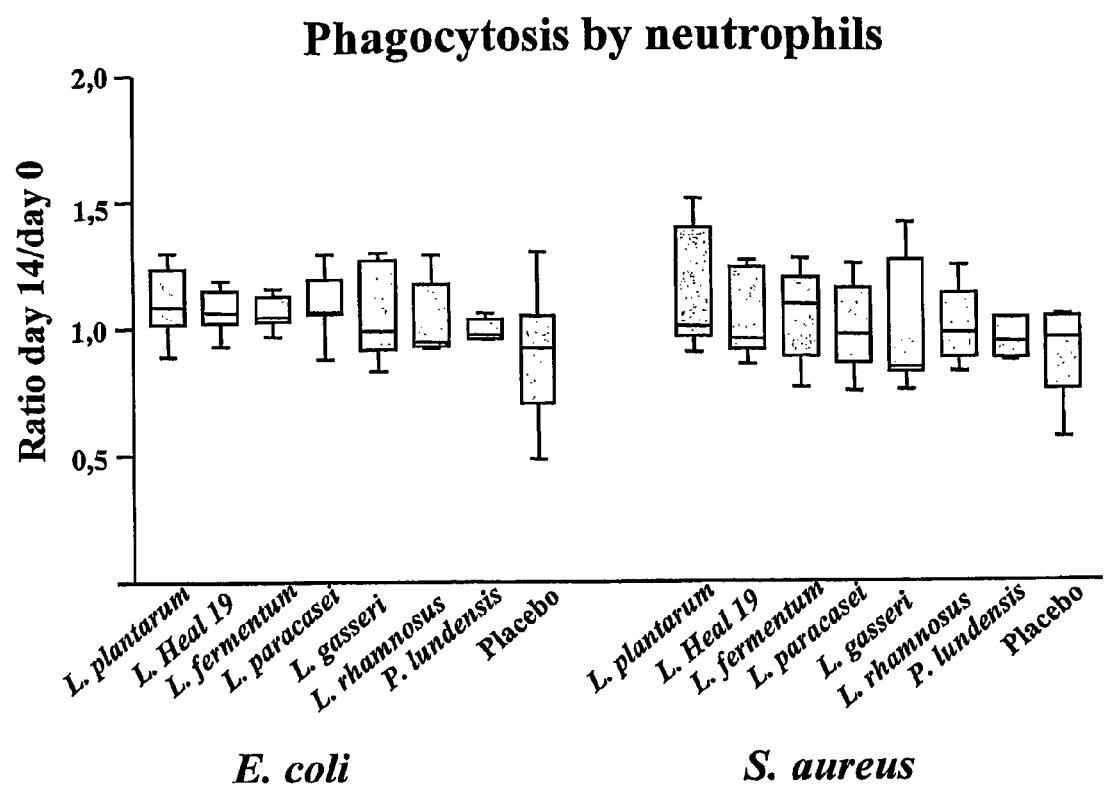
FIG. 8. The phagocytic activity of neutrophils was analysed by incubating whole blood cells with FITC-labelled *E. coli* or *S. aureus*. The ratio between mean fluorescence values obtained at day 14 and day 0 was determined individually and group calculations are shown in this figure.
Figure 9:
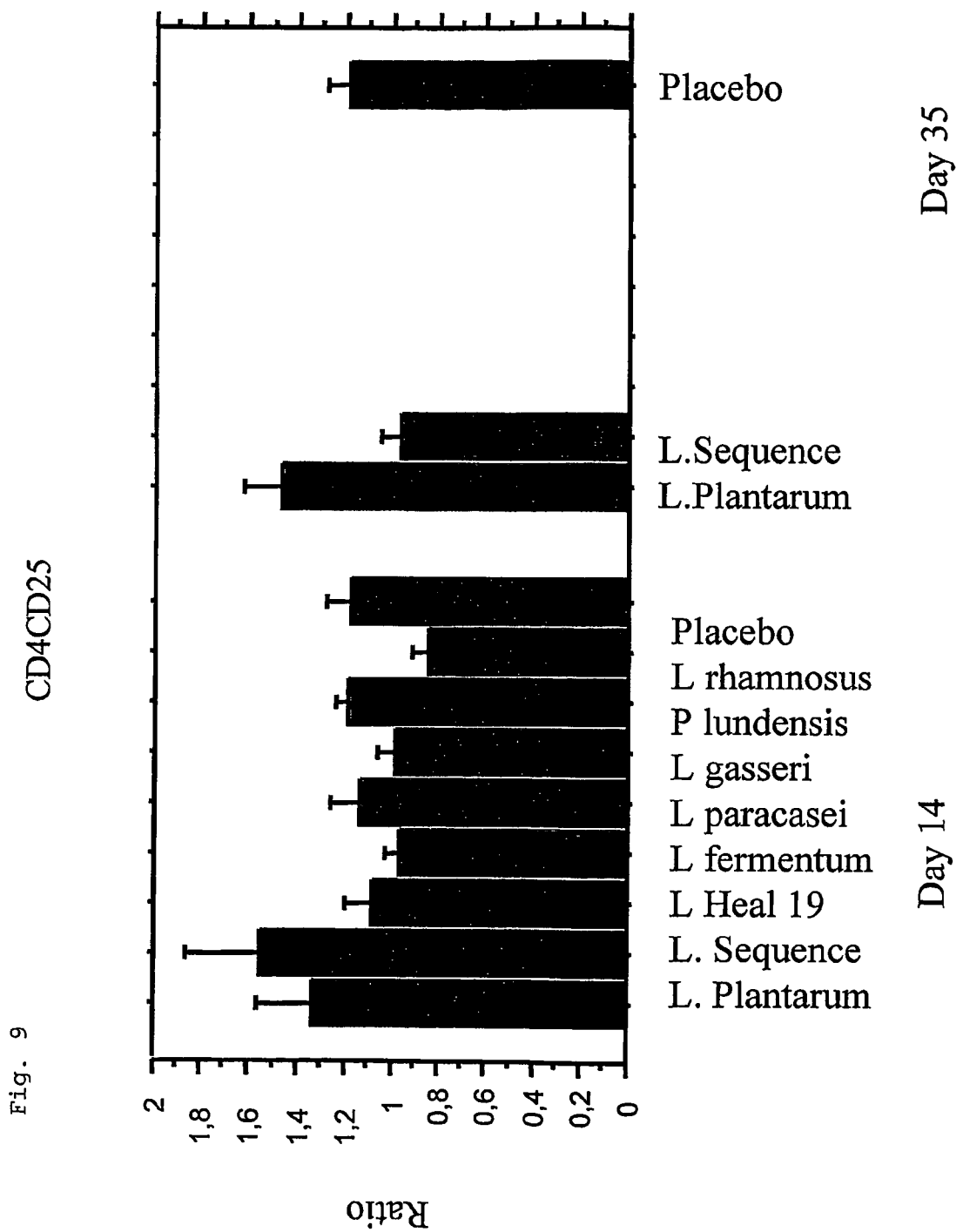
FIG. 9 shows the ratio of lymphocytes expressing the activation phenotypes CD4CD25 from experiment 2.
Figure 10:
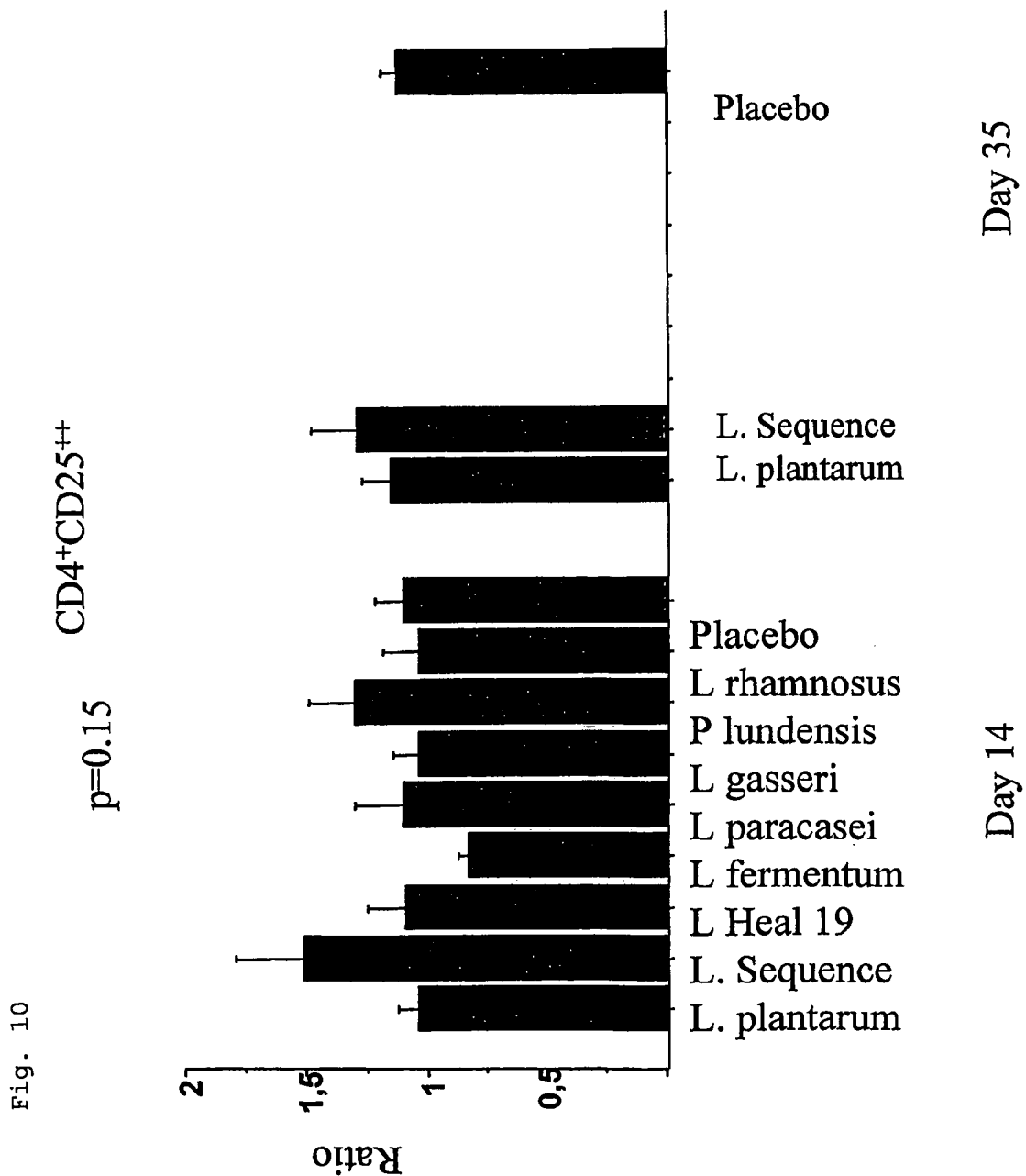
FIG. 10 shows the ratio of lymphocytes expressing the activation phenotypes CD4$^+$CD25$^{++}$ from experiment 2.
Figure 11:
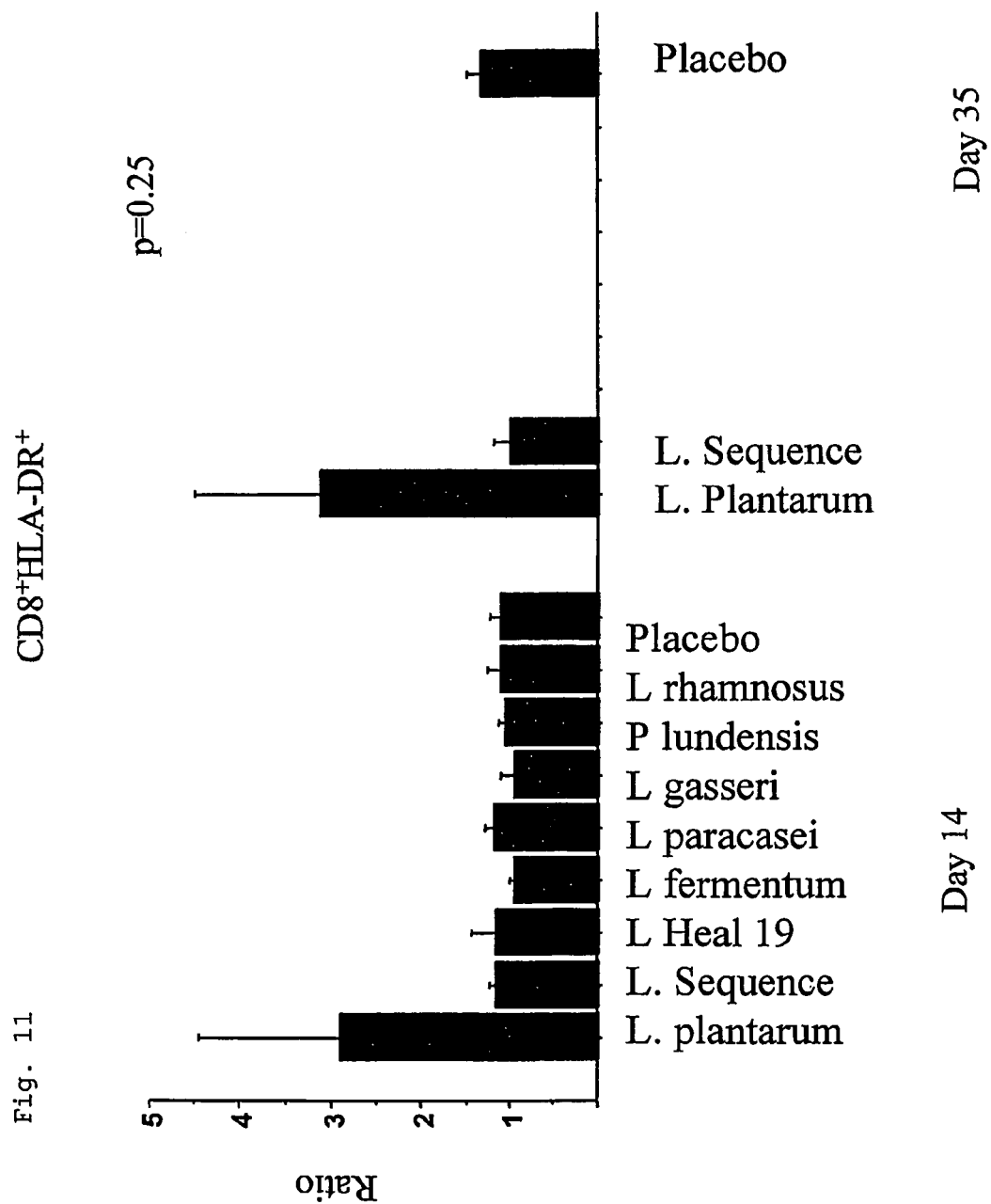
FIG. 11 shows the ratio of lymphocytes expressing the activation phenotypes CD8$^+$HLA-DR$^+$ from experiment 2.
Figure 12:
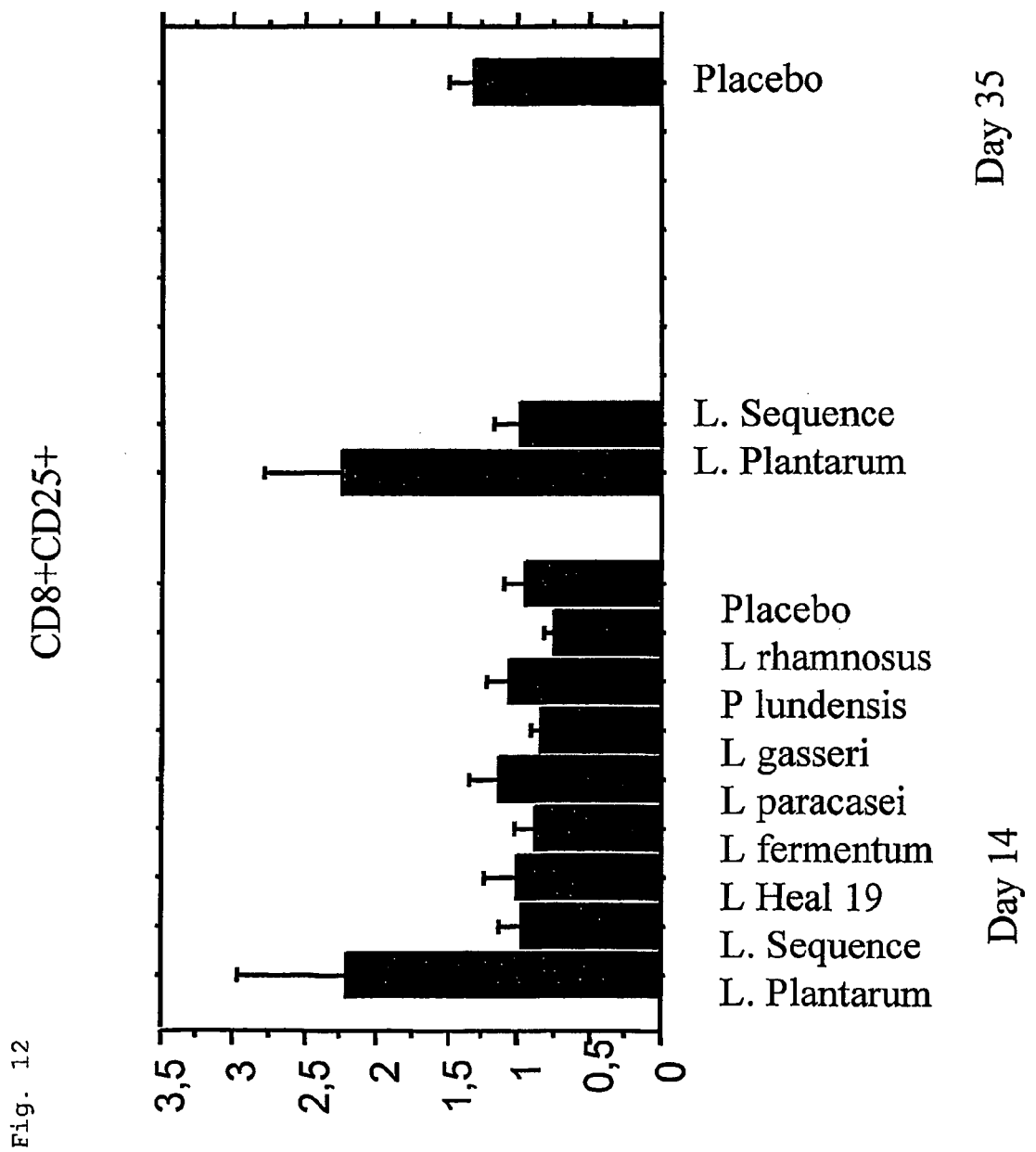
FIG. 12 shows the ratio of lymphocytes expressing the activation phenotypes CD8+CD25+ from experiment 2.

Granulocytes and monocytes were identified in the FSC-SSC diagram. The ability of these cells to phagocytose FITC-labelled Gram-positive or Gram-negative bacteria was tested. As shown in FIG. 8, granulocytes from volunteers given *L. plantarum* 299v (p=0.064), *L. plantarum* Heal 19 (p=0.064), *L. fermentum* (p=0.064) or *L. paracasei* (p=0.05) were more efficient then granulocytes from placebo treated volunteers in phagocytosis of the Gram-negative bacteria *E. coli*. However, there was no difference between the groups in phagocytosis of the Gram-positive bacteria *S. aureus*. No differences in the phagocytic activity of monocytes could be detected (data not shown).

Discussion

The primary task of the immune system is to react rapidly and violently to micro-organisms thereby preventing and curing infections. The killing of microorganisms employs powerful mechanisms that also cause harm to our own tissues. Therefore, it is necessary that it neither reacts to our own tissues, nor to innocuous substances present in the environment. Therefore, the immune system develops and maintains tolerance both to the components of our own body, and to food and inhaled proteins. If this fails, a number of diseases may arise. Means to develop specific immune tolerance are an essential task of the immune system.

A central role in all immune reactions is played by the T helper cell. When a T helper cell becomes activated by its specific antigen, it becomes activated, divides, matures and produces a range of cytokines which direct the action of other types of cells in the immune system, such as cytotoxic T cells and B cells. Activation of T helper cells is necessary in order to produce most types of immune reactions, including production of antibodies. Conversely, if activation of T helper cells is prevented, most types of immune reactions are paralysed.

There are several mechanisms by which activation of T helper cells and maintenance of tolerance is ensured. One mechanism is elimination in the thymus of T cells with capacity to recognize and react to own tissue. However, this elimination is not complete and, furthermore, we also need to develop specific immune tolerance to exogenous antigens. Otherwise we would react violently to all types of inhaled and ingested substances, leading to massive inflammation and wasted immune resources.

A cell type that is central for maintenance of tolerance is the regulatory T cell. This cell type can be recognized by certain markers, such as surface expression of CD4 and CD25, possession of intracellular CTLA-4, and transcription of the nuclear protein Foxp3. The regulatory T cells are capable of preventing other T cells to become activated when encountering harmless substances and, hence, prevent all types of unwanted immune reactions.

In the present context the symbol "+" in connection with a certain marker such as CD4+ and CD25+ means that the marker is expressed on a T cell. For instance CD4+CD25+ T cells are T cells that express both the CD4 marker and CD25 marker on its surface. However, nothing is said about the amount of the marker that is expressed, only that it is present. In the present context the symbol "++" in connection with a marker such as CD4++ or CD25++ means that there is a lot of marker expressed. The regulatory T cells are those cells with a lot of CD25 on the surface, i.e. CD4+CD25++ cells. On the other hand, CD4+CD25+ T cells are only activated T cells. Sometimes the specific symbols "+" and "++" are not used, e.g. CD4CD25 only, and this means that the cells are activated such CD4+CD25+ cells. Thus, CD4CD25 is the same as CD4+CD25+. When discussing regulatory T cells, it is always written as CD4+CD25++ cells.

This blind placebo-controlled study is unique in that it is the first study comparing the influence of several immune parameters following intake of different Gram-positive lactobacilli or the Gram-negative bacteria *P. lundensis*. Interestingly, intake of *P. lundensis* did not influence any of the measured parameters. In contrast, intake of lactobacilli affected different components of both the specific and innate immune system. A novel finding in this study was that intake of *L. plantarum* had a pronounced positive effect on activation and induction of memory cells in the T cell populations. There was a significant upregulation of the IL-2 receptor α chain (CD25) and a strong tendency towards upregulation of HLA-DR on cytotoxic T cells. A tendency towards upregulation of these activation markers was also observed on helper T cells after intake of *L. plantarum*. Expression of activation markers indicates that the T cells have started to proliferate in response to antigen-specific or non-specific stimuli and that these cells more readily exert their effector functions compared to resting T cells. The mechanisms behind *L. plantarum* induced activation of T cells could be via antigen presenting cells that are activated by toll-like receptors binding to microbial compounds. Activation of antigen presenting cells makes them more efficient in presenting antigen to T cells. In addition, both helper and cytotoxic T cells have shown to have various expressions of toll-like receptors, which probably make these cells sensible for non-specific activation by microbial components and products.

In analogy to the helper T cell compartment, expression of CD45RO seems to mark a memory population also among cytotoxic T cells. There was found a significant increase in the expression of this memory cell marker on helper T cells, and a tendency towards upregulation on cytotoxic T cells following 35 days intake of *L. plantarum*. In addition, intake of *L. paracasei* also showed a tendency towards upregulation of CD45RO on cytotoxic T cells. Relative to naïve T cells, CD45RO+ T cells can secrete a broad spectrum of cytokines. Moreover, CD45RO+ T cells can proliferate and produce IL-2 when the CD3-TCR complex is stimulated under suboptimal conditions, whereas naïve T cells require a strong CD3-TCR stimulus to carry out these functions. The formation of memory T cells is important for induction of an efficient immune response after infection and vaccination.

The innate cellular immune system was also affected by intake of probiotic bacteria. It was demonstrated that the natural killer T (NKT) cell population was expanded following intake of *L. paracasei*. NKT cells constitute a lymphocyte subpopulation that coexpress the NK cell marker CD56 and the T cell marker CD3-T cell receptor complex. Studies in both humans and mice have demonstrated that NKT cells play a central role in the regulation of autoimmune diseases, such as multiple sclerosis, type I diabetes, and systemic lupus. NKT cells also exert effector functions against tumour and virus infected cells. Thus, NKT cells are pleotropic in their functions. Other clinical studies evaluating the immunological effects of probiotic bacteria have shown that intake of *L. rhamnosus* HN001 and *Bifidobacterium lactis* HN019 enhance NK (including NKT) cell tumour killing activity of K562 cells. In this study it was also confirmed the observation by others that phagocytic activity of polymorphonuclear cells is increased after intake of different lactobacilli. The consequence of the observed effects on the different immune parameters in the present study is that one could speculate that the coincident activation of cytotoxic T cells and NKT cell expansion points to a strengthened immune defense against viral infections and/or tumours. The in vitro finding that lactobacilli induce mononuclear cells to secrete IL-12 and IL-18, supports the theory that intake of these bacteria stimulates cell-mediated activity.

In accordance with the present invention it has been concluded that intake of *L. plantarum* and *L. paracasei* has a profound effect on the specific and innate cellular immune system. However, the increase in immune function demonstrated herein is for the time being difficult to correlate to a proven health benefit in humans. In order to address this specific issue, further clinical trials in individuals suffering from e.g. viral infections or tumours need to be accomplished. In such studies, it would be of special interest to compare the effect of administration of *L. plantarum* and *L. paracasei* separately or in combination.

Example 2

The goal of this example was to investigate the effect on the immune system by giving the same species of lactobacilli for a longer period of time compared to several lactobacilli (different species) administered in a sequence one after the other.

The volunteers were given a powder with freeze-dried bacteria during 14 or 35 days. As gram-positive bacteria the probiotic bacteria *Lactobacillus plantarum* 299v is used alone or in combination with *L. rhamnosus, L. fermentum, L. paracasei*, and *L. gasseri*. As gram-negative bacteria *Pseudomonas lundensis* is given.

The following groups are studied:
1) *Lactobacillus plantarum* 35 days
2) *L. plantarum* 7d, *L. rhamnosus* 7d, *L. fermentum* 7d, *L. paracasei* 7d, *L. gasseri* 7d. Totally 35 days. (Sequence)
3) A mixture of *L. plantarum, L. rhamnosus, L. fermentum, L. paracasei, L. gasseri*. Totally 14 days
4) *L. rhamnosus* 14 days
5) *L. fermentum* 14 days
6) *L. paracasei* 14 days
7) *L. gasseri* 14 days
8) *Pseudomonas lundensis* 14 days
Control group 1) Placebo 35 days
Control group 2) Placebo 14 days Blood samples are taken at day 0, 14 and 35. The amount of helper T cells (CD4+) expressing high amounts of CD25 was defined in each group by flow cytometry as have been explained above in experiment 1.

Results

On day 14, there was a borderline significance of CD4+ CD25++ T cells being expanded in individuals consuming the sequence of five different lactobacilli strains.

Discussion

T helper cells (CD4+) expressing high density of the CD25 molecule (CD4+CD25++) have been shown to be important in order to protect against autoimmune diseases, allergies and inflammatory bowel diseases. The finding that these cells are expanded after intake of a sequence of different lactobacilli indicate that intake of these bacteria might be beneficial for the individual concerning the risk of developing the above mentioned diseases.

Experiment 3

The aim of the present study is to investigate whether intake of the lactic acid bacteria in a freeze-dried formula/functional food product during at least 3 months influences the severity of symptoms and the incidence and duration of common cold.

It is important that this is carried out in vivo in humans, as neither in vitro studies nor animal studies would reflect the degree of efficacy when administered to humans. The ability of these bacteria to become established in the intestine when administered directly after cultivation is documented in earlier studies.

Thus, the objective is to investigate if consumption of a mixture of $Lactobacillus\ plantarum$ 299v (DSM 9843) and $Lactobacillus\ paracasei$ 8700:2 (DSM 13434) ($1\times10^9$ cfu/d) can reduce the risk for common cold.

The study will take place during 90 days and 500 individuals will take part in the study. 250 individuals will receive the active product and 250 individuals will be given a placebo.

The study will be randomized, double blind and placebo-controlled with two parallel arms.

Exclusion criteria are as follows: Known intolerance or allergy to any ingredient included in the formulations; allergy medically treated; Current treatment for severe gastrointestinal disorders; Pregnancy or lactation; Vaccination against influenza within the last 12 months; and smokers.

The probiotic given: Lyophilized $Lactobacillus\ plantarum$ 299v and $Lactobacillus\ paracasei$ 8700; 2. Sucrose, maltodextrine and hydrolysed gelatine are added as cryoprotectants. Dosage will be a daily intake of 1 g lyophilized Lactobacilli (approximately $1\times10^9$ cfu/day). The dose is taken in association with breakfast.

The products will be produced, packed and labelled by Probi AB, Lund, Sweden. The quality of the product will also be checked by Probi AB. Each sachet will be labelled with the name of the study, the best by date, how they are to be stored, the name of the manufacturer, the name of the responsible investigator and her/his telephone number. In addition to the above information, a number denoting the subject is added on the secondary package. A detailed instruction for dissolution and intake will be inserted in the secondary package. The product will be supplied in sachets.

From day—14 to day 104, the subject may not ingest products containing probiotic bacteria. The subject will be provided with a list of probiotic products not allowed to be consumed during the study period.

Faecal samples are to be handed in on days 1 (before intake of study product), 15 (after intake), and 104 (after intake). The samples should be collected in two tubes no more than 18 hours before being handed in for analysis, and during this period are to be stored in a refrigerator. The samples will be analysed for lactobacilli.

Blood samples are to be taken day 1 and 15. The samples will be analyzed for CD4+ and CD8+.

In view of experiments 1 and 2 it is expected that an enhanced protection against common cold will be seen in the individuals taking the probiotic mixture compared to the placebo group.

The invention claimed is:

1. A method for the treatment of a common cold virus infection, said method comprising
   administering to a human a composition comprising at least one $Lactobacillus$ strain selected from the group consisting of $Lactobacillus\ plantarum$ HEAL 9, DSM 15312, $Lactobacillus\ plantarum$ HEAL 19, DSM 15313, $Lactobacillus\ plantarum$ HEAL 99, DSM 15316, $Lactobacillus\ paracasei$ 8700:2, DSM 13434, and $Lactobacillus\ paracasei$ 02A, DSM 13432.

2. The method of claim 1, wherein at least two of said strains of probiotic bacteria are administered.

3. The method of claim 2, wherein said strains are administered in a sequence.

4. The method of claim 2, wherein the strains are administered simultaneously.

5. The method of claim 1, wherein said composition is a liquid formulation or a solid formulation.

6. The method of claim 1, wherein said composition is a solid formulation and is chosen from the group consisting of tablets, sucking tablets, sweets, chewing tablets, capsules, sachets, powders, granules, coated particle and coated tablets, enterocoated tablets and capsules and melting strips and films.

7. The method of claim 1, wherein said composition is a liquid formulation and is selected from the group consisting of oral solutions, suspensions, emulsions and syrups.

8. The method of claim 5, wherein said composition comprises a carrier material.

9. The method of claim 8, wherein said carrier material is chosen from the group consisting of oat meal gruel, lactic acid fermented foods, resistant starch, dietary fibres, carbohydrates, proteins, and glycosylated proteins.

10. The method according to claim 5, wherein said composition is chosen from the group consisting of a food composition, a dietary supplement, a functional food, a medical food and a nutritional product.

11. The method according to claim 10, wherein said food composition is chosen from the group consisting of beverages, yoghurts, juices, ice creams, breads, biscuits, cereals, health bars, spreads, and nutritional products.

12. The method according to claim 5, wherein each of said strain(s) is present in the composition in an amount from about $1\times10^6$ to about $1\times10^{14}$ CFU.

13. The method according to claim 5, wherein each of said strain(s) is present in the composition in an amount from about $1\times10^8$ to about $1\times10^{12}$ CFU.

14. The method according to claim 5, wherein each of said strain(s) is present in the composition in an amount from about $1\times10^9$ to about $1\times10^{11}$ CFU.

15. The method according to claim 5, wherein at least two of said strains are present in the composition.

16. The method according to claim 5, wherein at least two compositions each comprising at least one of said strains are administered in a sequence.

* * * * *